(12) United States Patent
Bernecker et al.

(10) Patent No.: US 6,569,414 B1
(45) Date of Patent: May 27, 2003

(54) HAIR CONDITIONERS FOR TREATING SPLIT ENDS

(75) Inventors: Ullrich Bernecker, Huertgenwald (DE); Claudia Brockmann, Duesseldorf (DE); Detlef Hollenberg, Erkrath (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/508,585

(22) PCT Filed: Sep. 5, 1998

(86) PCT No.: PCT/EP98/05631
§ 371 (c)(1),
(2), (4) Date: Jun. 23, 2000

(87) PCT Pub. No.: WO99/13821

PCT Pub. Date: Mar. 25, 1999

(30) Foreign Application Priority Data

Sep. 13, 1997 (DE) .......................................... 197 40 285

(51) Int. Cl.⁷ ............................ A61K 7/06; A61K 7/11; A01N 25/00
(52) U.S. Cl. ................ 424/70.15; 424/70.1; 424/70.11; 514/938
(58) Field of Search ............................... 424/70.1, 70.11, 424/70.15; 514/938

(56) References Cited

U.S. PATENT DOCUMENTS 4,900,545 A    2/1990    Wisotzki et al. .............. 424/70

FOREIGN PATENT DOCUMENTS

| DE | 37 11 841 | 10/1988 |
| DE | 44 40 315 | 5/1996 |
| DE | 195 14 268 | 10/1996 |
| DE | 196 13 567 | 10/1997 |
| EP | 0 287 876 | 10/1988 |
| WO | WO96/14824 | 5/1996 |
| WO | WO96/32926 | 10/1996 |

*Primary Examiner*—Thurman K. Page
*Assistant Examiner*—Humera N. Sheikh
(74) *Attorney, Agent, or Firm*—Stephen D. Harper; Gregory M. Hill; Glenn E. J. Murphy

(57) ABSTRACT

The present invention relates to a hair treatment preparation and a method of use thereof. The hair treatment preparation is in the form of an oil-in-water emulsion and is preferably used for reducing split ends. The hair treatment preparation contains a lipid soluble ester alcohol or ester polyol and a water-soluble compound selected from panthenol, a panthenol derivative, nicotinic acid amide, a sugar, polyvinyl pyrrolidine or mixtures thereof.

16 Claims, No Drawings

HAIR CONDITIONERS FOR TREATING SPLIT ENDS

BACKGROUND OF THE INVENTION

This application is a 371 of PCT/EP98/05631 filed Sep. 5, 1998.

This invention relates to hair treatment preparations in the form of an oil-in-water emulsion containing a particularly effective combination of lipid-soluble and water-/soluble active substances capable of reducing split ends.

Split ends/are a phenomenon which manifests itself in the hair fibers becoming porous and in splitting of the individual hairs from their ends. Split ends are caused inter alia by severe mechanical stressing of the hair, for example by frequent brushing, back-combing or combing against high combing resistance. High combing resistance in dry hair can be caused by damage to the hair surface, static charging or tackiness attributable to residues of hair sprays. The danger of split ends is also increased by weakening of the hair structure which can be caused by frequent or careless application of chemical treatments, as for example in permanent waving or coloring.

Accordingly, there has been no shortage of attempts to regenerate hair damaged by split ends by applying suitable preparations, i.e. to stop the advance of split ends and to repair the split hairs.

DE 195 14 268 describes cosmetic preparations containing ester polyols which, when applied to the hair, are capable of increasing its tear strength. There is no reference in this document to the regeneration of split ends.

DE 37 11 841 A1 discloses hair-regenerating preparations which contain, for example, panthenol or glucose, optionally in combination with polyvinyl pyrrolidone, as water-soluble active substances for reducing split ends.

It was known from DE 44 40 315 A1 that combinations of mono- or oligosaccharides and derivatives thereof with cationically derivatized panthenol are capable of regenerating split hairs.

Although the last of the compositions mentioned above reduces the number of split ends in damaged hair, the effect is not entirely satisfactory in the case of products which are rinsed off from the hair after application (so-called rinse-off products), such as for example shampoos and hair rinses.

Accordingly, the problem addressed by the present invention was distinctly to improve hair treatment preparations in regard to their effectiveness in repairing split ends. This problem has to be solved to a particularly high degree by the split-end-regenerating hair treatment preparations according to the invention.

DESCRIPTION OF THE INVENTION

The present invention relates to hair treatment preparations in the form of an oil-in-water emulsion, characterized in that they contain 0.1 to 10% by weight of a lipid-soluble ester alcohol or ester polyol obtainable by reacting an epoxyfatty acid ester with a mono- or polyhydric alcohol containing 1 to 6 carbon atoms as a component of the oil phase and 0.1 to 3% by weight of a known, split-end-reducing water-soluble compound from the group consisting of panthenol, nicotinic acid amide, sugar, polyvinyl pyrrolidone or mixtures thereof as a component of the aqueous phase as ingredients active in reducing split ends.

Preparations in the context of the invention are both leave-on products, such as setting lotions, styling aids and hair conditioners, and rinse-off products, i.e. products which are rinsed off from the hair after application, such as for example shampoos, hair aftertreatments, permanent wave fixing lotions or, for example, hair colorants.

The only important requirement is that the preparations contain an emulsified oil phase, i.e. are present in the form of an oil-in-water emulsion or microemulsion.

The lipid-soluble ester alcohols or ester polyols are known from the literature and are commercially obtainable products. They may be regarded as lipid-soluble when 5% by weight of these products dissolve clearly in cetyl alcohol at 80° C.

The ester alcohols or ester polyols suitable for use in accordance with the invention are obtainable by reacting an epoxyfatty acid ester with water or mono- or polyhydric alcohols containing 1 to 10 carbon atoms which opens the epoxide ring and forms a vicinal dihydroxyethyl or hydroxyalkoxyethyl group. The epoxy fatty acid ester may even be an epoxidation product of a technical fatty acid ester containing saturated fatty acids. However, the epoxide oxygen content should be at least 3% by weight and is preferably in the range from 5 to 10% by weight.

The epoxyfatty acid esters are either epoxidized fatty acid esters of monohydric alcohols, i.e. for example epoxidized oleic acid methyl ester, linoleic acid methyl ester, ricinoleic acid methyl ester, or epoxidized fatty acid esters of polyhydric alcohols, for example glycerol monooleate or propylene glycol monooleate, or epoxidized fatty acid triglycerides, for example oleic acid triglyceride, or unsaturated oils such as, for example, olive oil, soybean oil, sunflower oil, linseed oil, rapeseed oil.

Of particular technical interest are, above all, unsaturated fatty acid methyl ester epoxides of unsaturated vegetable fatty acids. Thus, a particularly preferred ester polyol is the reaction product of a vegetable oil fatty acid methyl ester epoxidate with a polyol containing 2 to 6 carbon atoms and 2 to 6 hydroxyl groups. The polyols present may be, for example, ethylene glycol, 1,2-propylene glycol, 1,3-propylene glycol, butanediol, pentanediol, hexanediol, glycerol, trimethylol propane, pentaerythritol, sorbitol or diglycerol.

The reaction product of a vegetable fatty acid methyl ester epoxidate with trimethylol propane with a hydroxyl value of 350 to 450 is a particularly suitable ester polyol for the hair treatment preparation according to the invention. One such product based on soya fatty acid methyl ester epoxide and trimethylol propane is commercially obtainable as Sovermol®.

The present invention also relates to the use of ester polyols obtainable by reacting epoxyfatty acid esters having an epoxide oxygen content of at least 3% by weight with water or a mono- or polyhydric alcohol containing 1 to 10 carbon atoms as lipid-soluble substances active in reducing split ends in combination with water-soluble split-end-reducing compounds in hair treatment emulsions.

Known water-soluble split-end-reducing compounds which may be present are, for example, sugars, i.e. mono- and disaccharides. Suitable monosaccharides are, for example, glucose, fructose, mannose and deoxy sugars such as, for example, fucose or rhamnose. Suitable disaccharides are, for example, sucrose, cellobiose, lactose or maltose.

Another water-soluble compound active in reducing split ends is nicotinic acid amide which is preferably used in a quantity of 0.01 to 1% by weight. Nicotinic acid amide, also known as vitamin B3, has been described as a topical deodorant and also as a topical agent for preventing hair loss. Effectiveness in reducing split ends when externally applied to hair has not hitherto been observed.

Other known water-soluble split-end-reducing agents are panthenol and derivatives thereof, for example the cationically derived Panthequat® (CTFA name: Panthenyl-hydroxypropyl-steardimoniumchloride) and polyvinyl pyrrolidone. These water-soluble compounds are preferably used in combination. The hair treatment preparations according to the invention preferably contain 1 to 2% by weight of a sugar and 0.1 to 1% by weight of panthenol.

A combination of panthenol and nicotinic acid amide is also preferably present as water-soluble active substance in the preparations according to the invention. The ratio by weight between these two water-soluble "antisplit" agents may be between 1:1 and 10:1.

The hair treatment preparations according to the invention may additionally contain any of the usual auxiliaries and carrier components typically used for the particular application.

These are first and foremost the oil and fatty components and emulsifiers required for emulsion-like preparations.

The oil or fatty components normally used are paraffins or paraffin oils, natural or synthetic fatty acid esters, silicone oils, fatty alcohols or di-n-alkyl ethers. For hair aftertreatment preparations, $C_{14-22}$ fatty alcohols for example, more particularly cetyl and stearyl alcohol, are greatly preferred fatty components. However, fatty acid esters such as, for example, isopropyl myristate, n-hexyl laurate or n-decyl oleate, synthetic triglycerides such as, for example caprylic/capric acid triglyceride or natural triglycerides such as, for example, refined vegetable oils are also used for such purposes.

Preferred oil components for the production of microemulsions are the di-n-alkyl ethers, for example di-n-octyl ether.

Suitable emulsifiers are anionic, zwitterionic, cationic or nonionic surfactants. The cationic surfactants have the advantage that they counteract the static charging of hair and, in doing so, contribute towards improving combability and reducing split ends.

In addition, it is known that cationic surfactants are suitable for the production of very low-viscosity fatty alcohol dispersions and that quantities of only 0.1 to 1 part by weight of cationic quaternary ammonium surfactants are sufficient for stabilizing a dispersion of 10 to 25 parts by weight of cetyl or stearyl alcohol.

Mixtures of paraffin oils, fatty alcohols and optionally fatty acid esters are preferably used as oil components. In such cases, mixtures of cationic and nonionic surfactants are also generally used as emulsifiers. Suitable cationic surfactants are, for example, cetyl trimethyl ammonium chloride and distearoyloxyethyl hydroxyethyl methyl ammonium methoxysulfate. Suitable nonionic emulsifiers are, for example, products of the addition of 10 to 30 moles ethylene oxide onto $C_{16-22}$ fatty alcohols, fatty acid monoglycerides, sorbitan fatty acid monoesters or methyl glucoside fatty acid monoesters. Other suitable nonionic emulsifiers are, for example, fatty acid polyglycerol esters and mixtures thereof with methyl glucose fatty acid esters or alkyl (oligo) glycosides. The latter are preferably used for the production of microemulsions of the oil-in-water type.

In addition, fatty acid mono- or diglycerides, sorbitan fatty acid esters or propylene glycol monofatty acid esters, for example, are used as oil-soluble co-emulsifiers.

In addition, the emulsions may be viscosity-adjusted, i.e. thickened, with the water-soluble polymers and cellulose derivatives normally used for this purpose. Anionic polymers should not be used in combination with cationic surfactants because of possible interaction. Nonionic polymeric thickeners, for example methyl hydroxypropyl cellulose, hydroxypropyl guar, polyvinyl pyrrolidone and hydroxyethyl starch, are preferably used.

Other auxiliaries which may be present in the hair treatment preparations according to the invention to develop special hair-care effects are, for example, structurants, for example maleic acid, setting polymers, hair-conditioning compounds, for example phospholipids, for example soya lecithin, kephalins, silicone oils, proteins or protein hydrolyzates, cationic water-soluble polymers, quaternized protein hydrolyzates, plant extracts, allantoin, pyrrolidone carboxylic acid salts, vitamins, antidandruff agents such as, for example, Zinc Omadine, Piroctone Olamine, salicylic acid and other antimycotic agents active against Pityrosporum ovale, light filters (UV absorbers), hair dyes or dye precursors, oxidizing agents for permanent wave fixing, for example alkali metal bromates, hydrogen peroxide.

The emulsions may additionally contain the usual carriers and formulation aids necessary for stability, viscosity, appearance, odor and application, for example solvents and solubilizers, for example lower alcohol, glycols, glycerol, diethylene glycol, polyethylene glycol, dyes, opacifiers and pearlizers, pH regulators and buffers, for example citric acid/stearate, complexing agents, for example acetophosphonates, EDTA or NTA, preservatives, for example pheoxyethanol, p-hydroxybenzoates, perfumes, antioxidants and aerosol propellent gases.

The following Examples are intended to illustrate the invention.

EXAMPLES

The following formulations were prepared (Table 1):

TABLE I

| Composition | 1 | 2 | C1 |
|---|---|---|---|
| Sovermol ® 760 (1) | 0.5 | 0.25 | — |
| Paraffin oil, low viscosity | 33.5 | 3.5 | 3.5 |
| Cetyl/stearyl alcohol | 4.8 | 4.8 | 4.8 |
| Dehyquart ® F75 (2) | 0.35 | 0.35 | 0.35 |
| Cutina GMS (3) | 0.3 | 0.3 | 0.3 |
| Tego Care 450 (4) | 0.4 | 0.4 | 0.4 |
| PHB propyl ester | 0.2 | 0.2 | 0.2 |
| PHB methyl ester | 0.2 | 0.2 | 0.2 |
| Phenoxyethanol | — | 0.5 | 0.5 |
| Dehyquart A-CA (5) | 3.0 | 3.0 | 3.0 |
| Glucose monohydrate | 2.0 | 2.0 | 2.0 |
| d-Panthenol | — | 0.25 | 0.5 |
| Nicotinic acid amide | — | 0.1 | — |
| Culminal MHPC 3000 (6) | 0.6 | 0.6 | 0.6 |
| Perfume oil | 0.25 | 0.25 | 0.25 |
| Water | to 100 | to 100 | to 100 |

TABLE I-continued

| Composition | 1 | 2 | C1 |
|---|---|---|---|
| pH value | 3.5 | 4.25 | 3.7 |
| Viscosity [Pa · s], 20° C. (Brookfield, spindle 5, 4 rpm) | 54 | 53 | 30 |
| Split repair (%) R (corr.) | 20 | 41 | 14.3 |

The following commercial products were used:
(1) Sovermol® 760: reaction product of soya fatty acid methyl ester epoxide with 1 mole trimethylolpropane (per mole epoxide oxygen)
(2) Dehyquart® F75: mixture of ca. 70% distearyloxyethyl hydroxyethyl methyl ammonium methoxysulfate and ca. 30% cetearyl alcohol
(3) Cutina® GMS: glycerol (mono/di)stearate/palmitate, ca. 45% monoglyceride, ca. 40% diglyceride, ca. 10% triglyceride, ca. 2% glycerol
(4) Tego Care 450: polyglycerol(3)/methylglucose distearate
(5) Dehyquart A-CA: cetyl trimethylammonium chloride
(6) Culminal® MHPL 3000: methyl hydroxypropyl cellulose (viscosity 2% in water (20° C): ca. 3 Pa.s)

Production:

The components of the oil phase (Sovermol 760, paraffin oil, cetyl/stearyl alcohol, Dehyquart F75, Cutina GMS, Tego Care 450, PHB ester and phenoxyethanol) were heated together to 80° C. Ca. 60% of the water with the Dehyquart A-CA dissolved therein—also heated to 80° C.—were emulsified in the melt with stirring. A solution of glucose monohydrate, optionally panthenol and nicotinic acid amide in ca. 20% of the water and a "swelling" of Culminal MHPC in the remaining water were then added to and mixed while stirring with the emulsion at 40° C. The emulsion was then stirred at 30° C.

The pH value and the viscosity were measured after storage for 20 hours at 20° C.

Testing of the Split Repairing Effect

Bunches of hairs which had been seriously split by mechanical and electrostatic pretreatment (dry combing) were treated for 15 minutes with the undiluted preparations of Examples 1, 2 and C1, rinsed with tap water (16° dH) and then dried. The number of split ends was determined by counting before the treatment ($S_o$) and after the treatment ($S_b$) and the repairing effect was determined in accordance with the following equation:

$$R = \frac{S_o - S_b}{S_o} \cdot 100 \ [\%]$$

Since pure water has a repairing effect by this method of R=30%, the split repairing effect of the test products was corrected as follows:

$$R_{(corr.)} = \frac{R - 30}{70} \cdot 100 \ [\%]$$

The split repair values $R_{(corr.)}$ obtained are shown in Table I.

What is claimed is:

1. A hair treatment preparation in the form of an oil-in-water emulsion, comprising:
   0.1% to 10% by weight of a lipid-soluble ester alcohol or ester polyol, obtainable by reacting an epoxy fatty acid ester with water or a mono- or polyhydric alcohol containing 1 to 10 carbon atoms, as a component of the oil phase; and
   0.1% to 3% by weight of a water-soluble compound selected from the group consisting of panthenol, a panthenol derivative, nicotinic acid amide, a sugar, polyvinyl pyrrolidone, and mixtures thereof as a component of the aqueous phase, wherein the preparation is effective in treating split ends of hair to reduce the split ends, provided that the aqueous phase comprises at least panthenol and nicotinic acid amide.

2. The preparation of claim 1, wherein the ester polyol comprises a reaction product of a vegetable oil fatty acid methyl ester epoxidate with a polyol containing 2 to 6 carbon atoms and 2 to 6 hydroxyl groups.

3. The preparation of claim 1, wherein the ester polyol comprises a reaction product of a vegetable oil methyl ester epoxidate with trimethylol propane having a hydroxyl value of 350 to 450.

4. The preparation of claim 1, wherein the epoxyfatty acid ester has an epoxide oxygen content of at least 3% by weight, based on the weight of the epoxyfatty acid ester.

5. The preparation of claim 4, wherein the epoxyfatty acid ester has an epoxide oxygen content of 5% to 10% by weight, based on the weight of the epoxyfatty acid ester.

6. The preparation of claim 1, comprising 0.01% to 1% by weight nicotinic acid amide.

7. The preparation of claim 1, comprising 1% to 2% by weight of a sugar or mixture thereof.

8. The preparation of claim 1, comprising 0.1% to 1% by weight of panthenol.

9. The preparation of claim 1 comprising panthenol and nicotinic acid amide in a weight ratio of 1:1 to 10:1.

10. A hair treatment preparation in the form of an oil-in-water emulsion, comprising
   0.1% to 10% by weight of a lipid-soluble ester alcohol or ester polyol, obtainable by reacting an epoxyfatty acid ester having an epoxide oxygen content of at least 3% by weight based on the epoxyfatty acid ester with water or a mono- or polyhydric alcohol containing 1 to 10 carbon atoms, as a component of the oil phase; and
   0.1% to 1% by weight of panthenol and 0.01% to 1% by weight of nicotinic acid amide as components of the aqueous phase.

11. A method of treating split ends comprising the steps of:
   a) preparing an oil-in-water emulsion comprising (i) 0.1% to 10% by weight of a lipid-soluble ester alcohol or ester polyol, obtainable by reacting an epoxy fatty acid ester having an epoxide oxygen content of at least 3% by weight based on the epoxy fatty acid ester with water or a mono- or polyhydric alcohol containing 1 to 10 carbon atoms, as a component of the oil phase, and (ii) 0.1% to 3% by weight of a water soluble compound selected from the group consisting of panthenol, a panthenol derivative, nicotinic acid amide, a sugar, polyvinyl pyrrolidone, and mixtures thereof as a component of the aqueous phase, provided that the aqueous phase comprises at least panthenol and nicotinic acid amide; and
   b) applying the emulsion to hair and split ends in an amount effective to reduce the split ends.

12. The method of claim 11, wherein the ester polyol comprises a reaction product of a vegetable oil fatty acid methyl ester epoxidate with a polyol containing 2 to 6 carbon atoms and 2 to 6 hydroxyl groups.

13. The method of claim 11, wherein the ester polyol comprises a reaction product of a vegetable oil methyl ester epoxidate with trimethylol propane having a hydroxyl value of 350 to 450.

14. The method of claim 11, wherein the epoxyfatty acid ester has an epoxide oxygen content of at least 3% by weight, based on the weight of the epoxyfatty acid ester.

15. The method of claim 11, wherein the emulsion comprises 0.01% to 1% by weight of nicotinic acid amide and 0.1% to 1% by weight of panthenol.

16. The method of claim 15, wherein the weight ratio of panthenol to nicotinic acid amide is 1:1 to 10:1.

* * * * *